(12) United States Patent
Martikka et al.

(10) Patent No.: US 7,803,117 B2
(45) Date of Patent: Sep. 28, 2010

(54) METHOD, DEVICE AND COMPUTER PROGRAM PRODUCT FOR MONITORING THE PHYSIOLOGICAL STATE OF A PERSON

(75) Inventors: Mikko Martikka, Vantaa (FI); Erik Lindman, Espoo (FI)

(73) Assignee: Suunto Oy, Vantaa (FI)

( * ) Notice: Subject to any disclaimer, the term of this patent is extended or adjusted under 35 U.S.C. 154(b) by 932 days.

(21) Appl. No.: 11/432,380

(22) Filed: May 12, 2006

(65) Prior Publication Data

US 2007/0265534 A1    Nov. 15, 2007

(51) Int. Cl.
*A61B 5/02* (2006.01)
(52) U.S. Cl. .................. 600/483; 600/484; 600/500; 600/501; 600/503
(58) Field of Classification Search ........... 600/509, 600/301, 300, 483, 500–502, 484
See application file for complete search history.

(56) References Cited

U.S. PATENT DOCUMENTS

| | | | | |
|---|---|---|---|---|
| 4,966,155 | A * | 10/1990 | Jackson | 600/484 |
| 5,620,463 | A * | 4/1997 | Drolet | 607/3 |
| 5,630,463 | A * | 5/1997 | Shimmell | 164/312 |
| 5,810,722 | A | 9/1998 | Heikkila | |
| 5,921,929 | A * | 7/1999 | Goll et al. | 600/438 |
| 6,030,342 | A * | 2/2000 | Amano et al. | 600/301 |
| 6,081,742 | A * | 6/2000 | Amano et al. | 600/513 |
| 6,206,837 | B1 * | 3/2001 | Brugnoli | 600/529 |
| 6,361,501 | B1 * | 3/2002 | Amano et al. | 600/500 |
| 6,537,227 | B2 | 3/2003 | Kinnunen et al. | |
| 6,616,613 | B1 * | 9/2003 | Goodman | 600/504 |
| 7,460,901 | B2 | 12/2008 | Kettunen et al. | |
| 2004/0152957 | A1 * | 8/2004 | Stivoric et al. | 600/300 |
| 2005/0054938 | A1 | 3/2005 | Wehman et al. | |
| 2007/0208262 | A1 * | 9/2007 | Kovacs | 600/509 |
| 2008/0139952 | A1 * | 6/2008 | Kuroda et al. | 600/508 |

FOREIGN PATENT DOCUMENTS

| WO | WO-03/099114 A1 | 12/2003 |
|---|---|---|
| WO | WO 3099114 A1 * | 12/2003 |
| WO | WO-2004/073494 A2 | 9/2004 |

OTHER PUBLICATIONS

Indirect EPOC Prediction Method Based on Heart Rate Measurement, White paper by Firstbeat Technologies Ltd., pp. 1-5, (May 2005).
EPOC Based Training Effect Assessment, White paper by Firstbeat Technologies Ltd., pp. 1-5, (Sep. 2005).
VO2 Estimation Method Based on Heart Rate Measurement, White paper by Firstbeat Technologies Ltd., pp. 1-3, (Feb. 2005).

* cited by examiner

*Primary Examiner*—Robert L. Nasser, Jr.
*Assistant Examiner*—Michael D'Angelo
(74) *Attorney, Agent, or Firm*—Birch, Stewart, Kolasch & Birch, LLP

(57) ABSTRACT

The invention relates to a method, device, and computer program product for monitoring the physiological state of a person. In the method, the heartbeat of the person is detected in order to obtain a pulse signal, and at least one parameter depicting the respiration of the person is determined in the time domain with the aid of time stamps made of the basis of the pulse signal. With the aid of the method, it is possible to calculate an estimate of the person's energy consumption during exercise, without complicated calculations or preliminary data based on measurements.

2 Claims, 2 Drawing Sheets

METHOD, DEVICE AND COMPUTER PROGRAM PRODUCT FOR MONITORING THE PHYSIOLOGICAL STATE OF A PERSON

The present invention relates to the measurement and evaluation of physiological functions. More specifically, the invention relates to a method for estimating energy consumption and a device and computer program product for implementing the method.

U.S. Pat. No. 6,537,227 discloses one method for estimating energy consumption. In the method, the heart rate of the person and pre-entered reference parameters depicting the performance of the person are utilized, on the basis of which the energy consumption during performance is estimated. The calculation requires information on the person's maximum oxygen consumption (VO2max). Estimating this accurately prior to performance is not simple, and an erroneous estimation may produce a large error in the calculation.

WO publication 2003/099,114 discloses another kind of calculation method, in which the respiratory frequency is calculated with the aid of changes in the frequency and a modulation function generated through a neural network. Such a calculation requires a large calculation and memory capacity, which increases the power consumption, size, and price of the device performing it. Further, in the energy consumption calculation described in the publication, which is based on respiratory frequency through a change in the frequency, information or an estimate is required on the respiratory volume value of the person, or on a corresponding personal physiological variable, which, in order to create an accurate energy consumption value, should be separately measured, for example, in an exercise test, for entering to the performing device.

WO publication 2004/073,494 discloses a method for measuring energy consumption by exploiting the data of an acceleration sensor and a heart-rate meter. US publication 2005/054,938 discloses a method, in which further the data provided by an altimeter is utilized.

It is an aim of the invention to create an entirely new type of method for monitoring the physiological state, particularly the energy consumption of a person during exercise. In particular, the method is intended to create a method that can be implemented using a smaller computing capacity than in the known solutions.

In addition, it is an aim of the invention to create a new portable device for monitoring the state of a person during exercise, as well as a new computer program product.

The invention is based on the observation that respiratory frequency and/or other parameters relating to respiration can be derived directly from the pulse signal using the periodicity of the temporal variation of the pulse intervals (pulse interval noise) in the time domain.

In the method according to the invention, the heart rate of the person is measured in order to obtain a pulse signal comprising temporally successive pulse periods, or such measurement data is received from a suitable sensor, and, on the basis of the periodicity of the pulse interval noise, at least one parameter depicting the respiration of the person is determined directly in the time domain.

The device according to the invention for monitoring the physiological state of a person comprises means for measuring the heart rate, in order to detect temporally successive pulse periods, or means for receiving such a pulse signal. In addition, the device comprises means for defining at least one parameter depicting the person's respiration in the time domain, On the basis of the pulse interval noise of the pulse signal.

The computer program product according to the invention for defining the physiological state of a person is arranged to receive measurement data depicting the heart rate of the person and to determine, on the basis of the periodicity of the temporal variation of the heat-rate data contained in the measurement data, at least one parameter depicting the respiration of the person, on the basis of pulse detections in the time domain, with the aid of time stamps made.

Considerable advantages are obtained with the aid of the invention. Determination performed in the time domain, compared to analysis performed through a change in frequency, has the advantage of a reduced need for calculation. Thus the calculation is rapid and can be performed using small processor and program memory capacities, so that power consumption is also reduced and the device can be made cheaper. Low power consumption in turn means a longer operating time For the device and/or the possibility to use smaller batteries. Thus it is highly suitable for portable devices, such as wristop computers. The known methods based on frequency analysis typically use Fourier transformation, which makes the calculation complicated and requiring calculating power.

By using the invention it is also possible to achieve a sufficiently accurate estimate of energy consumption during exercise, without knowing the person's maximum oxygen or energy consumption. Thus the user need not perform an exercise test or similar test providing information on the user's metabolism, before monitoring of their personal energy consumption can commence. Experiments have shown that it is possible to achieve a mean error of even less than 15% in the estimation of energy consumption, without information on the person's real maximum oxygen consumption. The accuracy of the method is based on the successful determination of respiratory frequency.

The method also does not necessitate calculation of the momentary or mean pulse frequency, but rather the contribution of respiration to the pulse signal can be determined directly, with the aid of the stamping of the pulses, which is described in greater detail later.

We use the term pulse period to refer to the period of time during which the heart actually beats, and during which there is a strong pulse signal variation in the electrically measured pulse signal, caused by the heartbeat. We use the term pulse interval to refer to the time between the successive pulse periods. Within this time there are variations (noise), which are mainly influenced by respiration. The periodic contribution to pulse interval noise made by respiration can be distinguished by the method according to the method The determination taking place in the time domain is characterized by the periodicity of the pulse interval noise being detected without a conversion of coordinates, for example, to the frequency plane. The determination in the time domain can be made by collecting, with the aid of signal analysis, time stamps made on the basis of the detected pulse periods, in order to detect the periodicity of the time stamp series.

We use the term parameter depicting the person's respiration to refer primarily to the respiratory frequency. However, by utilizing the basic idea of the invention together with preliminary data parameters depicting the person, it is also possible, however, to determine the magnitude of ventilation.

In the following, various embodiments of the invention are described with reference to the accompanying drawings.

Figure 1:
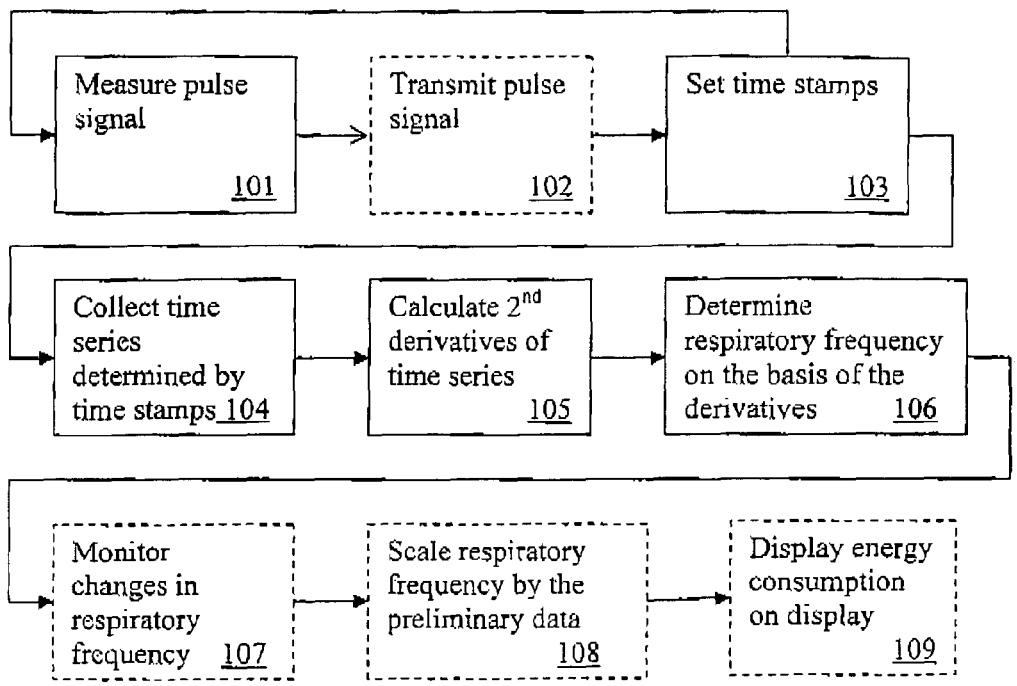
FIG. 1 shows a flow diagram of one embodiment of the present invention.
Figure 3:
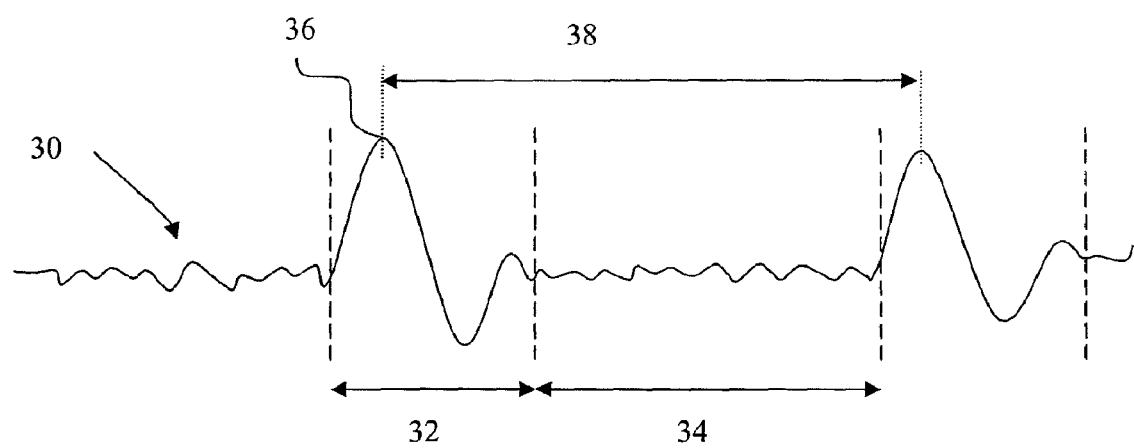
FIG. 3 shows part of a heart signal, by way of example.

FIG. 1 shows one possible way to implement the method according to the invention. The measurement 101 of the pulse signal takes place typically electrically using a pulse sensor, for example, a pulse belt secured around the chest, or with the aid of separate electrodes placed on the skin. The pulse signal is obtained by analyzing the heart signal, in order to detect the beats of the heart from the signal. The heart signal is illustrated in FIG. 3, in which the pulse period is marked with the reference number 32 and the rest period between the pulse periods with the reference number 34. A temporally well-defined point, such as the maximum or zero point of the signal (in FIG. 3, maximum point 36) is preferably detected from the pulse periods. Some method well known in the field can be used in the detection. In FIG. 3, the pulse interval defined by these points is marked with the reference number 38.

If necessary, the pulse signal is transferred, in stage 102, over a wire or wirelessly, from the pulse sensor to the terminal device, in which the method stages 103-108 described below can be implemented. As stated later, all the stages can also be performed in a single device.

In stage 103, time stamps corresponding to the heart bears are set on the basis of each individual signal. In stage 104, a number series for further analysis is formed form these time signals.

In stage 105, the period of the series is determined from the time series formed in stage 104. This can be found, for example, by calculating the second derivatives of the series and examining the zeros of this new series, i.e. the change points of the sign. One possible way to implement this stage of the method is described later in greater detail in Example 1.

In stage 106, some property correlating statistically with respiration, typically respiratory frequency, respiration amplitude, or the amount of air moved in respiration (ventilation), or several of these, are determined with the aid of the period of the series. An approximation of the respiratory frequency can be obtained directly on the basis of the period, whereas the calculation of the other variables typically requires preliminary data.

We have observed that the periodicity of the pulse interval noise utilized in the manner described above is a reliable indicator of respiration. A particularly advantageous feature of the method described is that from only the electrically measured pulse signal a respiration signal is also obtained with a good accuracy and by simple calculation taking place in the time domain. A relatively short period of time can be used as the monitoring interval, so that the parameter depicting respiration can also be updated reasonably quickly. When a new pulse is registered and time stamped, only a few calculation operations will be required to calculate the updated period. A typical monitoring interval of about 5-15 pulses at the pulse and respiration levels during exercise will provide a first approximation for the momentary respiratory frequency. If necessary, this can be made more precise, at the expense of the time resolution, by using a longer monitoring interval.

According to one highly preferred embodiment of the invention, a parameter depicting respiration is used to calculate energy consumption during exercise. In that case, typically at least one preliminary datum, either of the person who is the object of the measurement and/or of the sport being performed by him/her, will be used for assistance. The preliminary data comprise data that can be determined on the basis of tests or data that are not directly related to oxygen consumption. They can comprise, for example, the person's activity class, weight, height, or sex, or information on the nature of the sport being played by the person. The term nature of the sport refers primarily to whether the sport in question is a sprint-type sport or an endurance sport. The activity class (typically on a scale of 1-10) can, in turn, be determined on the basis of, for instance, the amount of training the person performs, without physical tests. Other personal or sport-specific data can also be used. In stage 108, the necessary calculation can be performed, always depending on the available preliminary data and known parameter/s depicting respiration. According to a greatly preferred embodiment, selected preliminary data are used directly as factors scaling the respiration parameter or parameters, which will further simplify and accelerate calculation. In the calculation, the preliminary data can be given various weights. The final result is preferably converted into absolute momentary values of energy consumption (e.g., kcal/min). The cumulative energy consumption of the exercise can also be calculated. The consumption can also be given as some relative values. In stage 109, the final result is displayed to the user.

Particularly in the starting or end stage of the exercise or other training, the respiratory frequency does not generally correlate directly with the energy consumption at that time. When a person starts exercise, their respiration does not immediately reach a level corresponding to the momentary energy consumption. On the other hand, at the end of the exercise, or during a break in it, the respiratory frequency will remain high, even though the physical stress is over. These factors can, however, be taken into account by monitoring the temporal change in the respiratory frequency, the heart rate, or some other measurable variable depicting the change in rhythm in the exercise. If, over a specified period of time, a change of a predefined magnitude is observed in such a variable, the respiratory frequency can be corrected by calculation towards a respiration-rate value that corresponds better to the actual energy consumption. A real-time correction can take place, for example, by keeping the momentary respiratory frequencies in the buffer memory at predefined monitoring intervals, and comparing the latest respiratory frequency received with the previous values. A more detailed depiction of the correction process can be implemented in the manner shown in Example 2, but one skilled in the art will understand that a calculation achieving a corresponding effect can be implemented in very many different ways.

The correction of the energy-consumption value is preferably boosted. This means that the energy-consumption values are corrected relatively more in relation to how much change occurs in the variable depicting the change in rhythm of the exercise. This compensates, for example, for the slow change in respiration or pulse, relative to the momentary intensity of exercise. The variable depicting the change in rhythm can, of course, also be, for example, information received through an acceleration sensor, in which case it may not be necessary to boost the correction.

Even though the present document describes the use of energy-consumption calculation and the correction calculation based on changes in respiratory frequency in connection with a respiratory-frequency determination taking place on a time domain, they can equally well be used in connection with other respiration-rate determination methods. Because the ways of calculation described can, however, also be implemented with a small computing capacity aid in real time, a particular advantage is achieved with their joint use.

The actual energy consumption is preferably calculated on the basis of the second-degree behaviour of the respiratory frequency, which has been observed to correspond well to the real energy consumption. Further, according to a preferred embodiment, in addition to respiratory frequency only general preliminary-data parameters that cannot be derived directly from metabolic tests concerning the person are used in the calculation, as described above. For example, height and weight (mass) are direct quantities according to SI units, which are easy to measure and are generally already known to the user with good accuracy. The activity class can be defined with the aid of existing widely used tables. These can be used directly as factors weighting the respiratory frequency or a secondary parameter calculated from it.

The known solutions approach the energy-consumption calculation problem from an entirely different direction; i.e. they measure or estimate the metabolism of the person, which is then used as a basis for the calculation of energy consumption. The present solution, on the other hand, is based on collecting sufficient general information the user, so that a estimate can be made of the assumed respiration-energy consumption dependence, This can also be regarded as being more reliable, in the sense that the effect on the final result of an individual erroneously entered preliminary-data factor is smaller than if, for example, an erroneously measured or entered VO2max measurement result is used as the basis of the calculation. Thus in the manner disclosed it is possible to create a way to calculate energy consumption that is both pleasant for the user and reliable.

Figure 2:
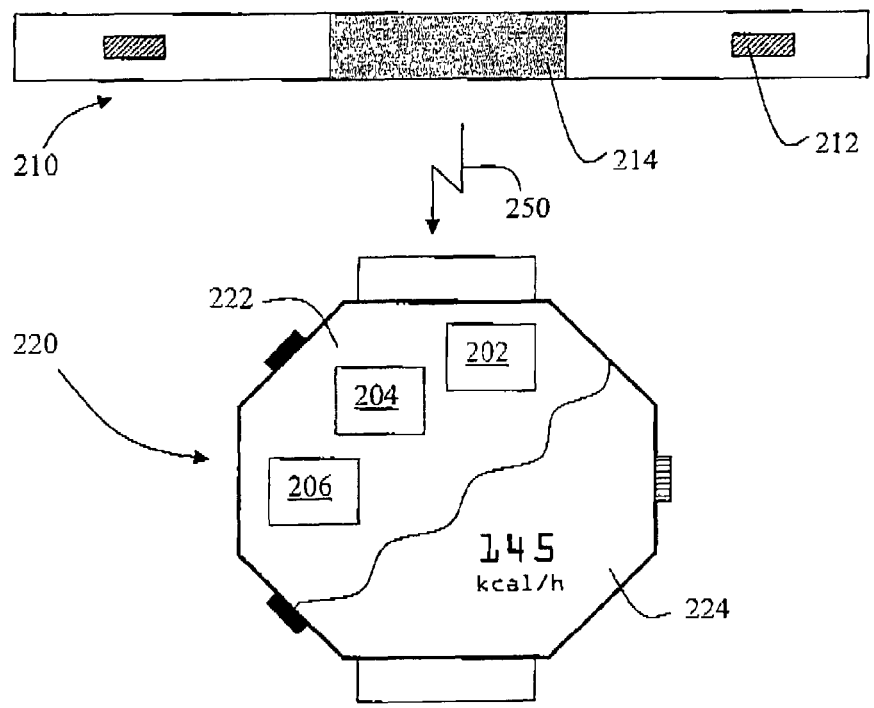
FIG. 2 shows a schematic diagram of one embodiment of the present device.

With reference to FIG. 2, the method disclosed is preferably performed either entirely or partly in a portable device, preferably in a wristop device 220. The measurement of the heart signal can be performed with the aid of a heart-rate belt 210, with the aid of the transmitter 214 in which the pulse signal is transferred by means of electromagnetic radiation 250 to the stop device 220. The transfer can take place inductively or with the aid of a radio-frequency signal. The measuring electrodes of the heart-rate belt are marked with the reference number 212. The wristop device 220 preferably comprises a pulse-signal receiver 202 and a processing unit 204 for setting the time stamps of the pulse-interval periods and for defining in the time domain at least one parameter depicting respiration, on the basis of the periodicity of the signal containing the pulse-interval periods of the pulse signal. In addition, the device has a buffer memory 206, for storing pulse data, the time-stamp series, and/or the calculated respiratory parameters. The signal processing of the pulse signal and the necessary other calculation are performed typically in a microprocessor, or in a separate microcircuit designed for these functions. The device can also have memory for the longer-term storage of pulse, respiration, and/or energy-consumption information. In addition, usually the device also has a display 224, in which the result of the calculation can be displayed.

Thanks to the method disclosed, the processing unit 204 can be made to be small and to consume little power.

The method can also be implemented in such a way that the calculation of the parameter depicting respiration can be performed either entirely or partly in the heart-rate belt or in some other sensor device, in which case the whole pulse signal need not be transferred to the terminal device. Thus, it is sufficient if only the final result of the calculation, or intermediate results together with their related time data are transferred at intervals to the terminal device.

The method can be implemented during exercise or also afterwards in a computer, to which the pulse signal or pulse data in the memory, the time stamps or intermediate results calculated from them, or derived parameters are transferred directly from the sensing device, or indirectly, for example, from a wristop computer.

The above detailed description of embodiments of the invention, the accompanying drawings, and the following examples, do not restrict the invention, but instead should be taken only as examples of ways to implement the invention in practice. The invention should be interpreted in the full extent of the Claims and taking the Doctrine of Equivalents into account.

EXAMPLE 1

This example illustrates how the respiratory frequency can be determined simply in the time domain from the pulse signal. The starting point is that the heartbeats have been detected from the pulse signal and with their aid a series of time points has been selected from the noise of the pulse-interval periods.

The time series picked out of the pulse signal and used in the calculation of the respiratory frequency and/or ventilation is a series of numbers, which consist of time points. Each time point corresponds to the moment when the heartbeat was detected. The time is measured, for example, in milliseconds.

This provides a monotonously increasing number series of moments in time (in milliseconds, for example, 0, 1010, 1950, 2800, 3650, . . . ), with the possible exception of the moment when as a result of the overflow of a variable containing time stamps the reading is recommenced from zero. The approximation of the first derivative of the signal strengths corresponding to this number series is $(t2-t1)/1 = sv1$. The approximation of the second derivative is $(sv2-sv1)/1$, in which $sv2=(t3-t2)/1$. By examining the moment of change pf the sign of the second derivative a new number series is obtained: tt1, tt2, tt3, . . . In this number series, tt1=–the moment in time, when the sign became positive (or negative)+the moment in time, when the sign became positive (or negative) for the following time. This time period depicts the periodicity of the pulse-interval noise, from which the respiratory frequency and ventilation can be approximated.

EXAMPLE 2

The correction of the respiratory frequency in order to take changes in the rhythm of the performance into account (Stages 1-6) and further the energy-consumption value (Stages 7-8) can be implemented for example, in the following manner:

1. Calculate the momentary respiratory frequency
2. Search for the global minimum of the respiratory frequency (in a specific period in time)
3. Search for the local maximum of the respiratory frequency (in a specific shorter period in time)
4. If the new respiratory frequency is sufficiently less than the local maximum (for example 15%), reduce the respiratory frequency by a coefficient 0 . . . 1 (for example 0.7)
5. If the new respiratory frequency sufficiently exceeds the local maximum (for example 20%), update the local maximum towards the latest respiration-rate value
6. Deduct a correction factor, which can be a fixed value or a value (offset correction) adapting with the aid of the global respiration-rate minimum, from the respiratory frequency pre-processed in Stages 1-5
7. Raise the respiratory frequency pre-processed in Stages 1-6 by the power of two
8. Scale the value obtained directly by the preliminary-data parameters.

The invention claimed is:

1. A method for monitoring the physiological state of a person during exercise using a portable computerized device, comprising:

monitoring the heartbeat of the person in order to obtain heartbeat pulse signals, each heartbeat pulse signal having a maximum and minimum value and a duration or period, and wherein a pulse interval exists between consecutive heartbeat pulse signals, and determining at least one parameter depicting the respiration of the person on the basis of the periodicity of the temporal variation of pulse data contained in the pulse interval, wherein the periodicity of the temporal variation of the pulse data is determined, using the portable computerized device, in the time domain by time stamping pulse signal data and using the time stamped pulse data, and the parameter depicting respiration is used to estimate energy consumption of the person, and further comprising estimating the energy consumption on the basis of a second degree behavior of the parameter representing respiration.

2. A portable device for monitoring the physiological state of a person during exercise, which device comprises:

a sensor for detecting heartbeat in order to create heartbeat pulse signals or means for receiving heartbeat pulse signals created with the aid of such sensor, each heartbeat pulse signal having a maximum and a minimum value and a duration or period, and wherein a pulse interval exists between consecutive heartbeat pulse signals, and a processing unit for defining at least one parameter depicting respiration, on the basis of the periodicity of the temporal variation of pulse data contained in the pulse interval, wherein the processing unit is adapted to determine the periodicity of the temporal variation of the pulse data by time stamping pulse signal data, and to estimate energy consumption of the person on the basis of the at least one parameter depicting respiration, wherein the device is adapted to estimate the consumption of energy on the basis of a second-degree behavior of respiration frequency.

* * * * *